United States Patent
Dochnahl et al.

(10) Patent No.: US 9,365,495 B2
(45) Date of Patent: *Jun. 14, 2016

(54) PROCESS FOR MANUFACTURING ARYLOXYACETAMIDES

(71) Applicants: Maximilian Dochnahl, Mannheim (DE); Michael Rack, Eppelheim (DE); Michael Keil, Freinsheim (DE); Bernd Wolf, Niederkirchen (DE); Uwe Josef Vogelbacher, Ludwigshafen (DE); Joachim Gebhardt, Wachenheim (DE); Timo Frassetto, Mannheim (DE); Volker Maywald, Ludwigshafen (DE)

(72) Inventors: Maximilian Dochnahl, Mannheim (DE); Michael Rack, Eppelheim (DE); Michael Keil, Freinsheim (DE); Bernd Wolf, Niederkirchen (DE); Uwe Josef Vogelbacher, Ludwigshafen (DE); Joachim Gebhardt, Wachenheim (DE); Timo Frassetto, Mannheim (DE); Volker Maywald, Ludwigshafen (DE)

(73) Assignee: BASF SE, Ludwigshafen (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/365,822

(22) PCT Filed: Dec. 20, 2012

(86) PCT No.: PCT/EP2012/076367
§ 371 (c)(1),
(2) Date: Jun. 16, 2014

(87) PCT Pub. No.: WO2013/092850
PCT Pub. Date: Jun. 27, 2013

(65) Prior Publication Data
US 2015/0119572 A1    Apr. 30, 2015

(30) Foreign Application Priority Data

Dec. 23, 2011 (EP) .................................. 11195503

(51) Int. Cl.
| | | |
|---|---|---|
| C07C 231/24 | (2006.01) |
| C07D 413/04 | (2006.01) |
| C07C 231/12 | (2006.01) |
| C07C 235/20 | (2006.01) |
| C07D 207/06 | (2006.01) |
| C07D 211/06 | (2006.01) |
| C07D 295/185 | (2006.01) |
| C07C 235/34 | (2006.01) |
| C07D 207/16 | (2006.01) |
| C07D 211/16 | (2006.01) |

(52) U.S. Cl.
CPC ............. *C07C 231/24* (2013.01); *C07C 231/12* (2013.01); *C07C 235/20* (2013.01); *C07C 235/34* (2013.01); *C07D 207/06* (2013.01); *C07D 207/16* (2013.01); *C07D 211/16* (2013.01); *C07D 295/185* (2013.01); *C07D 413/04* (2013.01)

(58) Field of Classification Search
None
See application file for complete search history.

(56) References Cited

FOREIGN PATENT DOCUMENTS

| | | |
|---|---|---|
| JP | 56-152448 | 11/1981 |
| JP | 58-52256 | 3/1983 |
| WO | WO 2006/060494 | 6/2006 |
| WO | WO 2010/145992 | 12/2010 |

OTHER PUBLICATIONS

International Preliminary Report on Patentability dated Jun. 24, 2014, prepared in International Application No. PCT/EP2012076367.
International Search Report dated Apr. 3, 2013, prepared in International Application No. PCT/EP2012076367.
Kirsanov, A.V., "Dimethylamides of alkoxydichloroacetic acids", Zhurnal obshchei khimii, Nauka, Moscow, Jan. 1, 1959, p. 100-1005, vol. 29.
Yagupolskii, L.M., "Reactions of (Aryloxy)-,(Arylthio)-, and (Arylsulfonyl)- Difluoroacetic esters with ammonia and amines", Journal of General Chemistry USSR, Consultants Bureau, New York, NY, 1969, p. 1711-1714, vol. 39, No. 8.
European Search Report dated May 16, 2012, prepared in corresponding European Application No. 11195503.

*Primary Examiner* — Samantha Shterengarts
(74) *Attorney, Agent, or Firm* — Brinks Gilson & Lione

(57) ABSTRACT

The present invention relates to a process for manufacturing aryloxyacetamides of formula (I),

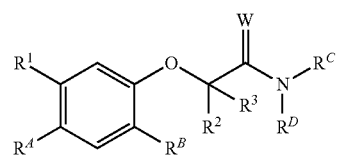

by reacting haloacetamides of formula (II) with a phenol of formula (III); wherein the variables are defined according to the description, and aryloxyacetamides of formula (I).

8 Claims, No Drawings

PROCESS FOR MANUFACTURING ARYLOXYACETAMIDES

This application is a National Stage application of International Application No. PCT/EP2012/076367, filed Dec. 20, 2012, the entire contents of which is hereby incorporated herein by reference. This application also claims priority under 35 U.S.C. §119 to European Patent Application No. 11195503.5, filed Dec. 23, 2011, the entire contents of which is hereby incorporated herein by reference.

The invention relates to aryloxyacetamides, a process for manufacturing these compounds, their use in and a process for manufacturing triazinon-benzoxazinones.

WO 2010/145992 discloses a synthesis of benzoxazinones by cyclization of N-aryl acetamides in the presence of DBU—a base that is rather expensive.

Hence, there is still room for improvement, specifically in view of economical and ecological aspects.

One task of the invention is to provide new useful intermediates for the synthesis of benzoxazinones and as well as a process for the preparation of said intermediates. A further task of the invention is to provide an improved process for manufacturing benzoxazinones.

According to WO 2006/060494, the treatment of 4-fluorophenol with sodium hydride and ethyl 2-bromo-2,2-difluoroacetate leads to the formation of the corresponding 2-aryl-2,2-difluoroacetic acid ethyl ester in 59%, whereas WO 2005/063767 discloses that the reaction of 3-bromo-4-nitrophenol with sodium hydroxide and ethyl 2-chloro-2,2-difluoroacetate gives the corresponding aryl difluoromethyl ether in 75% yield.

This suggests that the outcome of attempts to synthesize a 2-aryloxy-2,2-dihaloacetate from the phenol and a trihaloacetate strongly depends on the substrates and the reaction conditions.

It has been found that treating phenols with haloacetamides in the presence of a base leads to the formation of the corresponding aryloxyacetamides in high yields for a variety of substrates.

Accordingly, in one aspect of the invention there is provided a process for manufacturing aryloxyacetamides of formula (I),

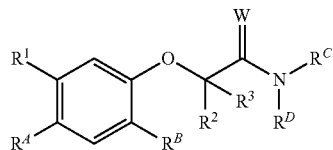

(I)

wherein
$R^1$ is H or halogen;
$R^2$ is halogen;
$R^3$ is H or halogen;
$R^A$ is H, halogen, $NH_2$ or $NO_2$;
$R^B$ is H, halogen, $NH_2$ or $NO_2$;
$R^C$, $R^D$ are independently of each other $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl or benzyl, wherein the phenyl and the benzyl ring are independently of one another unsubstituted or substituted with 1 to 5 substituents selected from the group consisting of halogen, $NO_2$, $C_1$-$C_6$-alkyl or $C_1$-$C_6$-alkoxy, or $R^C$ and $R^D$ together with the N atom which they are attached to, represent a saturated or aromatic 3- to 6-membered ring, optionally containing 1 to 3 additional heteroatoms from the group O, S and N, with the ring optionally being substituted with 1 to 3 $C_1$-$C_6$-alkyl substituents; and W is O or S;
wherein haloacetamides of formula (II),

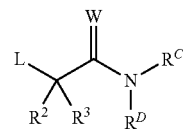

(II)

wherein $R^2$, $R^3$, $R^C$, $R^D$ and W are defined as in formula (I); and
L is halogen;
are reacted with phenols of formula (III),

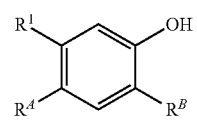

(III)

or a salt thereof,
wherein $R^1$, $R^A$ and $R^B$ are defined as in formula (I);
optionally in the presence of a base.

In a further aspect of the invention there is provided a process for manufacturing triazinon-benzoxazinones of formula (IV),

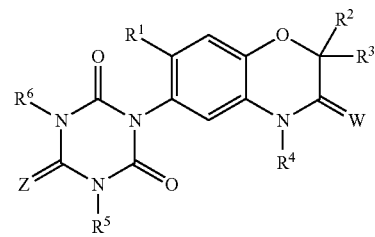

(IV)

wherein $R^1$, $R^2$, $R^3$ and W are defined as in formula (I);
$R^4$ is H, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
$R^5$ is H, $NH_2$, $C_1$-$C_6$-alkyl or $C_3$-$C_6$-alkynyl;
$R^6$ is H or $C_1$-$C_6$-alkyl; and
Z is O or S.

In a further aspect of the invention there are provided aryloxyacetamides of formula (I).

In a further aspect of the invention there is provided the use of aryloxyacetamides of formula (I) in manufacturing triazinon-benzoxazinones of formula (IV).

According to the invention the aryloxyacetamides of formula (I) are obtained in high yields and purities for a variety of substrates.

The phenols of formula (III) as described herein can also be employed in the form of their salts. Suitable are, in general, those salts of the phenols of formula (III), which cations have no adverse effect on the reaction.

Preferred cations are the ions of the alkali metals, preferably of lithium, sodium, potassium, rubidium and cesium, of the alkaline earth metals, preferably of magnesium, calcium and barium, of the elements boron, aluminum and tin, and of the transition metals, preferably of titanium, silver and zinc.

Especially preferred the phenols of formula (III) as described herein are employed in form of their alkali metal or alkaline metal salts.

Particular preference is given to the ions of alkali metals, preferably of sodium and potassium, and the alkaline earth metals, preferably magnesium and calcium.

Very particular preference is given to potassium cations.

The organic moieties mentioned in the definition of the variables according to the present invention, e.g. $R^1$ to $R^6$, $R^A$, $R^B$, $R^C$ and $R^D$ are—like the term halogen—collective terms for individual enumerations of the individual group members.

The term halogen denotes in each case fluorine, chlorine, bromine or iodine. All hydrocarbon chains, i.e. all alkyl, can be straight-chain or branched, the prefix $C_n$-$C_m$ denoting in each case the possible number of carbon atoms in the group.

Examples of such meanings are:

$C_1$-$C_4$-alkyl: for example $CH_3$, $C_2H_5$, n-propyl, $CH(CH_3)_2$ n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-cyanoalkyl, $C_1$-$C_6$-nitroalkyl, $C_1$-$C_6$-hydroxyalkyl, $C_1$-$C_6$-alkyoxy-$C_1$-$C_6$-alkyl, $C_3$-$C_6$-cycloalkyl-$C_1$-$C_4$-alkyl, amino-$C_1$-$C_6$-alkyl, ($C_1$-$C_6$-alkyl)amino-$C_1$-$C_6$-alkyl and di($C_1$-$C_6$-alkyl)amino-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, a $C_1$-$C_3$-haloalkyl radical as mentioned above, and also, for example, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl and also the cycloalkyl moieties of $C_3$-$C_6$-cycloalkyl-$C_1$-$C_6$-alkyl: monocyclic saturated hydrocarbons having 3 to 6 ring members, such as cyclopropyl, cyclobutyl, cyclopentyl and cyclohexyl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkenyl: $C_3$-$C_6$-alkenyl as mentioned above, and also ethenyl;

$C_3$-$C_6$-haloalkenyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_2$-$C_6$-alkynyl: $C_3$-$C_6$-alkynyl as mentioned above and also ethynyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

($C_1$-$C_4$-alkyl)amino: for example methylamino, ethylamino, propylamino, 1-methylethylamino, butylamino, 1-methylpropylamino, 2-methylpropylamino or 1,1-dimethylethylamino;

($C_1$-$C_6$-alkyl)amino and also the ($C_1$-$C_6$-alkyl)amino moieties of ($C_1$-$C_6$-alkyl)amino-$C_1$-$C_6$-alkyl: ($C_1$-$C_4$-alkylamino) as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino 3,3-dimethylbutylamino, 1-ethylbutylamino, 2-ethylbutylamino, 1,1,2-trimethylpropylamino, 1,2,2-trimethyl-propylamino, 1-ethyl-1-methylpropylamino or 1-ethyl-2-methylpropylamino;

di($C_1$-$C_4$-alkyl)amino: for example N,N-dimethylamino, N,N-diethylamino, N,N-di(1-methylethyl)amino, N,N-dipropylamino, N,N-dibutylamino, N,N-di(1-methylpropyl)amino, N,N-di(2-methylpropyl)amino, N,N-di (1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl) amino, N-(1,1-dimethylethyl)-N-methylamino, N-ethyl-N-propylamino, N-ethyl-N-(1-methylethyl) amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$-$C_6$-alkyl)amino and also the di($C_1$-$C_6$-alkyl)amino moieties of di($C_1$-$C_6$-alkyl)amino-$C_1$-$C_6$-alkyl: di($C_1$-$C_4$-alkyl)amino as mentioned above, and also, for example, N-methyl-N-pentylamino, N-methyl-N-(1-methylbutyl)amino, N-methyl-N-(2-methylbutyl) amino, N-methyl-N-(3-methylbutyl)amino, N-methyl-N-(2,2-dimethylpropyl)amino, N-methyl-N-(1-ethylpropyl)amino, N-methyl-N-hexylamino, N-methyl-N-(1,1-dimethylpropyl)amino, N-methyl-N-(1,2-dimethylpropyl)amino, N-methyl-N-(1-methylpentyl)amino, N-methyl-N-(2-methylpentyl)amino, N-methyl-N-(3-methylpentyl)amino, N-methyl-N-(4-methylpentyl)amino, N-methyl-N-(1,1-dimethylbutyl) amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl) amino, N-methyl-N-(3,3-dimethylbutyl)amino, N-methyl-N-(1-ethylbutyl)amino, N-methyl-N-(2-ethylbutyl)amino, N-methyl-N-(1,1,2-trimethylpropyl) amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methylpentyl) amino, N-ethyl-N-(3-methylpentyl)amino, N-ethyl-N-(4-methylpentyl)amino, N-ethyl-N-(1,1-dimethylbutyl) amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethylbutyl) amino, N-ethyl-N-(3,3-dimethylbutyl)amino, N-ethyl-N-(1-ethylbutyl)amino, N-ethyl-N-(2-ethylbutyl) amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

saturated or aromatic 3- to 6-membered ring optionally containing 1 to 3 additional heteroatoms selected from the group O, S and N:

a monocyclic, saturated or aromatic cycle having three to six ring members which comprises apart from one nitrogen atom and carbon atoms optionally additionally one to three heteroatoms selected from the group O, S and N, for example: 1-aziridinyl; 1-azetidinyl; 1-pyrrolidinyl, 2-isothiazolidinyl, 2-isothiazolidinyl, 1-pyrazolidinyl, 3-oxazolidinyl, 3-thiazolidinyl, 1-imidazolidinyl, 1,2,4-triazolidin-1-yl, 1,2,4-oxadiazolidin-2-yl, 1,2,4-oxadiazolidin-4-yl, 1,2,4-thiadiazolidin-2-yl, 1,2,4-thiadiazolidin-4-yl; 1-pyrrolyl, 1-pyrazolyl, 1-imidazolyl, 1,2,3-triazol-1-yl, 1,2,4-triazol-1-yl, 1-tetrazolyl; 1-piperidinyl, 1-hexahydropyridazinyl, 1-hexahydropyrimidinyl, 1-piperazinyl, 1,3,5-hexahydrotriazin-1-yl, 1,2,4-hexahydrotriazin-1-yl, tetrahydro-1,3-oxazin-1-yl, 1-morpholinyl.

The preferred embodiments of the invention mentioned herein below have to be understood as being preferred either independently from each other or in combination with one another.

According to a preferred embodiment of the invention preference is also given to the preparation of those aryloxyacetamides of formula (I), wherein the variables, either independently of one another or in combination with one another, have the following meanings:

$R^1$ is preferably H or F; particularly preferred H; is also preferably halogen, particularly preferred F or Cl, especially preferred F;

$R^2$ is preferably Cl or F, particularly preferred F;

$R^3$ is preferably H, Cl or F, particularly preferred H or F, especially preferred H; is also preferably halogen, particularly preferred F or Cl, especially preferred F;

$R^A$ is preferably H or $NO_2$; particularly preferred H; also particularly preferred $NO_2$;

$R^B$ is preferably H or $NO_2$; particularly preferred H; also particularly preferred $NO_2$;

$R^C$ and $R^D$ preferably are independently of each other $C_1$-$C_6$-alkyl, $C_1$-$C_6$-cyanoalkyl, $C_1$-$C_6$-hydroxyalkyl, $C_1$-$C_6$-alkoxy-$C_1$-$C_6$-alkyl, $C_3$-$C_6$-cycloalkyl, phenyl or benzyl, wherein the phenyl and the benzyl ring are independently of one another unsubstituted or substituted with 1 to 3 substituents selected from the group consisting of halogen, $C_1$-$C_6$-alkyl or $C_1$-$C_6$-alkoxy, or $R^C$ and $R^D$ together with the N atom which they are attached to, represent a saturated or aromatic 5- to 6-membered ring, optionally containing 1 additional heteroatom from the group O and N, with the ring optionally being substituted with 1 to 2 $C_1$-$C_6$-alkyl substituents;

particularly preferred are independently of each other $C_1$-$C_4$-alkyl, $C_1$-$C_4$-hydroxyalkyl, $C_1$-$C_6$-alkoxy-$C_1$-$C_4$-alkyl or benzyl, wherein the benzyl ring is unsubstituted or substituted by 1 to 3 substituents selected from the group consisting of halogen, $C_1$-$C_4$-alkyl or $C_1$-$C_4$-alkoxy, especially preferred the benzyl ring is unsubstituted, or $R^C$ and $R^D$ together with the N atom which they are attached to, represent a saturated 5- to 6-membered ring, optionally containing 1 additional oxygen atom, with the ring optionally being substituted with 1 to 2 $C_1$-$C_6$-alkyl substituents;

especially preferred are independently of one another $C_1$-$C_6$-alkyl or $R^C$ and $R^D$ together with the N atom which they are attached to, represent a saturated 5- to 6-membered ring optionally containing 1 additional oxygen atom;

more preferred are independently of one another $C_1$-$C_6$-alkyl;

W is preferably O,
is also preferably S.

In one embodiment of the invention $R^A$ and $R^B$ are H or $NO_2$;

preferably $R^A$ and $R^B$ are H or $NO_2$, wherein not both of $R^A$ or $R^B$ are $NO_2$;

particularly preferred $R^A$ is H and $R^B$ is H or $NO_2$, also particularly preferred $R^A$ is H or $NO_2$ and RB is H;

especially preferred $R^A$ and $R^B$ are H or also especially preferred $R^A$ is hydrogen and $R^B$ is $NO_2$;

also especially preferred $R^A$ is $NO_2$ and $R^B$ is H.

Particular preference is given to the preparation of aryloxy-acetamides of formula (Ia), which correspond to aryloxyacetamides of formula (I) wherein $R^1$, $R^2$ and $R^3$ are F and W is O:

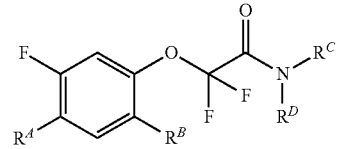

(Ia)

wherein the variables $R^A$, $R^B$, $R^C$ and $R^D$ have the meanings, in particular the preferred meanings, as defined above;

most preference to the preparation of aryloxyacetamides of formulae (Ia.1) to (Ia.27) of Table A listed below, in which the variables $R^A$, $R^B$, $R^C$ and $R^D$ together have the meanings given in one row of table A (aryloxyacetamides of formulae Ia.1 to Ia.27); and where the definitions of the variables $R^A$, $R^B$, $R^C$ and $R^D$ are of particular importance for the process and the compounds according to the invention not only in combination with one another but in each case also on their own:

TABLE A

| no. | $R^A$ | $R^B$ | $R^C$ | $R^D$ |
|---|---|---|---|---|
| Ia. 1. | H | H | $CH_3$ | $CH_3$ |
| Ia. 2. | H | H | $CH_2CH_3$ | $CH_2CH_3$ |
| Ia. 3. | H | H | H | $CH_3$ |
| Ia. 4. | H | H | $CH_3$ | $CH(CH_3)_2$ |
| Ia. 5. | H | H | —$CH_2$—$CH_2$—$CH_2$—$CH_2$— | |
| Ia. 6. | H | H | —$CH_2$—$CH_2$—$CH_2$—$CH_2$—$CH_2$— | |
| Ia. 7. | H | H | —$CH_2$—$CH_2$—O—$CH_2$—$CH_2$— | |
| Ia. 8. | H | H | —$CH_2$—$CH_2$—N($CH_3$)—$CH_2$—$CH_2$— | |
| Ia. 9. | H | H | —$CH_2$—CH($CH_3$)—O—CH($CH_3$)—$CH_2$— | |
| Ia. 10. | H | $NO_2$ | $CH_3$ | $CH_3$ |
| Ia. 11. | H | $NO_2$ | $CH_2CH_3$ | $CH_2CH_3$ |
| Ia. 12. | H | $NO_2$ | H | $CH_3$ |
| Ia. 13. | H | $NO_2$ | $CH_3$ | $CH(CH_3)_2$ |
| Ia. 14. | H | $NO_2$ | —$CH_2$—$CH_2$—$CH_2$—$CH_2$— | |
| Ia. 15. | H | $NO_2$ | —$CH_2$—$CH_2$—$CH_2$—$CH_2$—$CH_2$— | |
| Ia. 16. | H | $NO_2$ | —$CH_2$—$CH_2$—O—$CH_2$—$CH_2$— | |
| Ia. 17. | H | $NO_2$ | —$CH_2$—$CH_2$—N($CH_3$)—$CH_2$—$CH_2$— | |
| Ia. 18. | H | $NO_2$ | —$CH_2$—CH($CH_3$)—O—CH($CH_3$)—$CH_2$— | |
| Ia. 19. | $NO_2$ | H | $CH_3$ | $CH_3$ |
| Ia. 20. | $NO_2$ | H | $CH_2CH_3$ | $CH_2CH_3$ |
| Ia. 21. | $NO_2$ | H | H | $CH_3$ |
| Ia. 22. | $NO_2$ | H | $CH_3$ | $CH(CH_3)_2$ |
| Ia. 23. | $NO_2$ | H | —$CH_2$—$CH_2$—$CH_2$—$CH_2$— | |
| Ia. 24. | $NO_2$ | H | —$CH_2$—$CH_2$—$CH_2$—$CH_2$—$CH_2$— | |
| Ia. 25. | $NO_2$ | H | —$CH_2$—$CH_2$—O—$CH_2$—$CH_2$— | |
| Ia. 26. | $NO_2$ | H | —$CH_2$—$CH_2$—N($CH_3$)—$CH_2$—$CH_2$— | |
| Ia. 27. | $NO_2$ | H | —$CH_2$—CH($CH_3$)—O—CH($CH_3$)—$CH_2$— | |

With respect to the variables within the haloacetamides of formula (II), the particularly preferred embodiments of the haloacetamides of formula (II) correspond, either independently of one another or in combination with one another, to those of the variables of $R^2$, $R^3$, $R^C$, $R^D$ and W of formula (I), or have, either independently of one another or in combination with one another, the following meanings:

L is preferably Cl, Br or I, particularly preferred Cl or Br, especially preferred Br.

Particular preference is given to the haloacetamides of formula (IIa) (corresponds to haloacetamides of formula (II) wherein $R^2$ and $R^3$ are F and W is O),

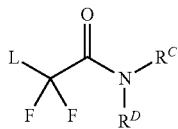

(IIa)

wherein the variables $R^C$, $R^D$ and L have the meanings, in particular the preferred meanings, as defined above;

most preference is given to the haloacetamides of formulae (IIa.1) to (IIa.18) of table B listed below, in which the variables $R^C$, $R^D$ and L together have the meanings given in one row of Table B (haloacetamides of formulae IIa.1 to IIa.18); and where the definitions of the variables $R^C$, $R^D$ and L are of particular importance for the process and the compounds according to the invention not only in combination with one another but in each case also on their own:

TABLE B

| no. | L | $R^C$ | $R^D$ |
|---|---|---|---|
| IIa.1. | Cl | $CH_3$ | $CH_3$ |
| IIa.2. | Cl | $CH_2CH_3$ | $CH_2CH_3$ |
| IIa.3. | Cl | H | $CH_3$ |
| IIa.4. | Cl | $CH_3$ | $CH(CH_3)_2$ |
| IIa.5. | Cl | —$CH_2$—$CH_2$—$CH_2$—$CH_2$— | |
| IIa.6. | Cl | —$CH_2$—$CH_2$—$CH_2$—$CH_2$—$CH_2$— | |
| IIa.7. | Cl | —$CH_2$—$CH_2$—O—$CH_2$—$CH_2$— | |
| IIa.8. | Cl | —$CH_2$—$CH_2$—$N(CH_3)$—$CH_2$—$CH_2$— | |
| IIa.9. | Cl | —$CH_2$—$CH(CH_3)$—O—$CH(CH_3)$—$CH_2$— | |
| IIa.10. | Br | $CH_3$ | $CH_3$ |
| IIa.11. | Br | $CH_2CH_3$ | $CH_2CH_3$ |
| IIa.12. | Br | H | $CH_3$ |
| IIa.13. | Br | $CH_3$ | $CH(CH_3)_2$ |
| IIa.14. | Br | —$CH_2$—$CH_2$—$CH_2$—$CH_2$— | |
| IIa.15. | Br | —$CH_2$—$CH_2$—$CH_2$—$CH_2$—$CH_2$— | |
| IIa.16. | Br | —$CH_2$—$CH_2$—O—$CH_2$—$CH_2$— | |
| IIa.17. | Br | —$CH_2$—$CH_2$—$N(CH_3)$—$CH_2$—$CH_2$— | |
| IIa.18. | Br | —$CH_2$—$CH(CH_3)$—O—$CH(CH_3)$—$CH_2$— | |

With respect to the variables within the phenols of formula (III), the particularly preferred embodiments of the phenols of formula (III) correspond, either independently of one another or in combination with one another, to those of the variables of $R^1$, $R^A$ and $R^B$ of formula (I).

Particular preference is also given to the phenols of formula (IIIa) (corresponds to phenols of formula (III) wherein $R^1$ is F),

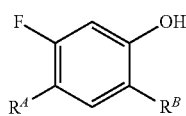

(IIIa)

wherein the variables $R^A$ and $R^B$ have the meanings, in particular the preferred meanings, as defined above;

most preference to the phenols of formulae (IIIa.1) to (IIIa.5) of table C listed below, in which the variables $R^A$ and $R^B$ together have the meanings given in one row of Table C (phenols of formulae IIIa.1 to IIIa.5); and where the definitions of the variables $R^A$ and $R^B$ are of particular importance for the process and the compounds according to the invention not only in combination with one another but in each case also on their own:

TABLE C

| no. | $R^A$ | $R^B$ |
|---|---|---|
| IIIa.1. | H | H |
| IIIa.2. | H | $NO_2$ |
| IIIa.3. | $NO_2$ | H |
| IIIa.4. | $NH_2$ | $NO_2$ |
| IIIa.5. | $NO_2$ | $NH_2$ |

In one preferred embodiment of the invention the phenol of formula (III) is employed.

In another preferred embodiment of the invention a salt of the phenol of formula (III) is employed.

The haloacetamides of formula (II) can be prepared by methods known in the art, e.g. by treatment of an available ester with the corresponding amine $NHR^CR^D$ or by transamidification of an available amide, see e.g. J. Med. Chem. 1999, 42, 2087. In line with this, the haloacetamide of formula (II) can be obtained from other carboxylic acid derivatives or the corresponding carboxylic acid.

The phenols of formula (III) or a salt thereof can be prepared by methods known in the art, see e.g. The chemistry of the hydroxyl group, S. Patai (ed.), Interscience, London, New York 1971.

A salt of the phenol of formula (III) may be obtained by treatment of the corresponding phenol with a suitable base.

The molar ratio of the phenol of formula (III) or a salt thereof, to the haloacetamide of formula (II) is generally in the range of 1:3 to 1:5, preferably 1:1.5 to 1:3, more preferably 1:1.02 to 1:1.05.

The reaction of the haloacetamide of formula (II) with the phenol of formula (III) or a salt thereof can optionally be carried out in presence of a base.

In one embodiment a salt of the phenol of formula (III) is employed, and the reaction of the haloacetamide of formula (II) with the salt of the phenol of formula (III) is carried out in the absence of a base.

In a preferred embodiment a phenol of formula (III) is employed, and the reaction of the haloacetamide of formula (II) with the phenol of formula (III) is carried out in the presence of a base.

Examples of suitable bases are carbonates such as lithium carbonate, sodium carbonate, potassium carbonate, cesium carbonate, magnesium carbonate, calcium carbonate, barium carbonate; hydrogen carbonates such as lithium hydrogen carbonate, sodium hydrogen carbonate, potassium hydrogen carbonate; hydroxides such as lithium hydroxide, sodium hydroxide, potassium hydroxide, magnesium hydroxide, calcium hydroxide, barium hydroxide, aluminum hydroxide; oxides such as lithium oxide, sodium oxide, potassium oxide, magnesium oxide, calcium oxide, barium oxide, iron oxide, silver oxide; hydrides such as lithium hydride, sodium hydride, potassium hydride, calcium hydride; phosphates such as potassium phosphate, calcium phosphate; alkoxides such sodium, potassium and magnesium alkoxides.

Preferred bases include potassium carbonate, potassium bicarbonate, potassium methoxide and potassium hydroxide.

More preferred bases include potassium carbonate and potassium methoxide.

Especially preferred bases are carbonates as defined above, in particular potassium carbonate.

The term base as used herein also includes mixtures of two or more, preferably two of the above compounds. Particular preference is given to the use of one base.

If a base is employed, the number of base equivalents with regard to the phenol of formula (III) is generally in the range of 1:0.5 to 1:10, preferably 1:0.6 to 1:5, more preferably 1:0.7 to 1:2.

Preferably, the reaction of the haloacetamide of formula (II) with the phenol of formula (III) or a salt thereof, and optionally in the presence of a base, is carried out in a solvent.

Examples of suitable solvents are dipolar aprotic solvents such as N,N-dimethylformamide (DMF), N,N-dimethylacetamide (DMAC), 1-methyl-2-pyrrolidinone (NMP), 1,3-dimethyl-2-imidazolidinone (DMI), N,N'-dimethylpropylene urea (DMPU), dimethyl sulfoxide (DMSO), sulfolane, acetonitrile, benzonitrile, acetone, methyl ethyl ketone, methyl butyl ketone, methyl isobutyl ketone, cyclohexanone, nitromethane, nitroethane, nitrobenzene; esters such as ethyl acetate, butyl acetate, isobutyl acetate; ethers such as diethylether, dibutylether, tert-butyl methyl ether (TBME), tetrahydrofurane (THF), cyclopentyl methyl ether, 1,4-dioxane; alcohols such as methanol, ethanol, isopropanol, 1-butanol, 2-butanol, isobutanol, tert-butanol, hexafluoro isopropanol; halogenated hydrocarbons such as dichloroethane, carbon tetrachloride; aliphatic hydrocarbons such as hexane, cyclohexane; aromatic hydrocarbons such as benzene, toluene, xylenes, mesitylene, chlorobenzene.

Preferred solvents include N,N-dimethylacetamide (DMAC), N,N-dimethylformamide (DMF), 1-methyl-2-pyrrolidinone (NMP) and 1,3-dimethyl-2-imidazolidinone (DMI).

More preferred solvents include N,N-dimethylacetamide (DMAC) and N,N-dimethylformamide (DMF).

The term solvent as used herein also includes mixtures of two or more of the above compounds.

In another embodiment of the invention, the haloacetamide of formula (II) is used as the solvent.

The reaction of the haloacetamide of formula (II) with the phenol of formula (III) or a salt thereof, and optionally in the presence of a base, is-generally carried out at a temperature in the range from 0 to 200° C., preferably in the range from 80 to 140° C., more preferably in the range from 90 to 130° C.

In one embodiment the haloacetamide of formula (II) is added to the phenol of formula (III) or a salt thereof.

In one embodiment a salt of the phenol of formula (III) is employed, and the haloacetamide of formula (II) is added to the salt of the phenol of formula (III), preferably in a solvent. The mixture is brought to a temperature in the range from 80 to 170° C., preferably 95 to 125° C., and stirred at the indicated temperature for 0.5 to 8 h, preferably 1 to 4 h.

In a further embodiment a salt of the phenol of formula (III) is employed, and the salt of the phenol of formula (III) is generated in situ at a temperature in the range from 0 to 200° C., preferably 0 to 150° C. Then the haloacetamide of formula (II) is added. The mixture is brought to a temperature in the range of 0 to 200° C., preferably 80 to 120° C., and stirred at the indicated temperature for 0.5 to 8 h, preferably 1 to 4 h.

In a preferred embodiment the phenol of formula (III) is employed, and the haloacetamide of formula (II), the phenol of formula (III), a base, and preferably a solvent are mixed together. The mixture is brought to a temperature in the range from 0 to 200° C., preferably 80 to 120° C., and stirred at the indicated temperature for 0.5 to 8 h, preferably 1 to 4 h.

After completion or partial completion of the reaction, the respective mixture can be worked up by means of standard techniques. Examples thereof include filtration, aqueous work-up and evaporation of solvents and/or other volatile compounds. These methods can also be combined with each other.

In one embodiment the crude product is used without further purification.

In another embodiment the crude product is purified, for example by fractional distillation or crystallization.

Aryloxyacetamides of formula (I-1) (corresponding to aryloxyacetamides of formula (I), wherein $R^A$ and $R^B$ independently from one another H or $NO_2$, and wherein at least one of $R^A$ and $R^B$ is H) are useful in the synthesis of dinitro compounds of formula (I-2) (corresponding to aryloxyacetamides of formula (I), wherein $R^A$ and $R^B$ are $NO_2$):

Dinitro compounds of formula (I-2) can be obtained by reacting aryloxyacetamides of formula (I-1) with $HNO_3/H_2SO_4$:

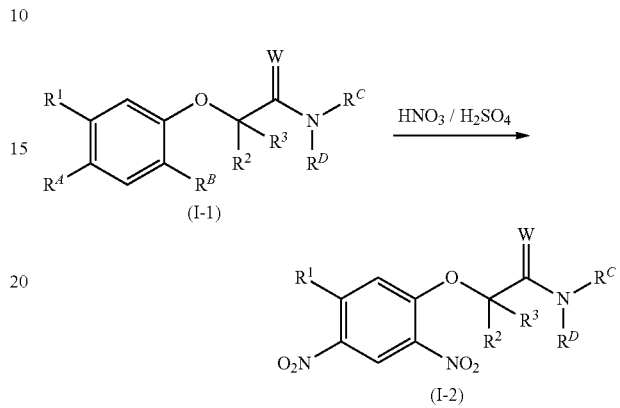

I wherein $R^A$ and $R^B$ are H or $NO_2$, I wherein $R^A$ and $R^B$ are $NO_2$ and wherein at least one of $R^A$ and $R^B$ is H Accordingly, in a further preferred embodiment of the process of the invention the dinitro compounds of formula (I-2) are prepared by i) reacting an haloacetamide of formula (II),

wherein $R^2$, $R^3$, $R^C$, $R^D$, W and L are defined as above; with a phenol of formula (III-1),

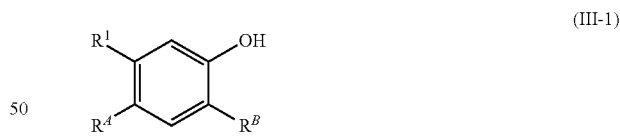

wherein $R^A$ and $R^B$ independently from one another H or $NO_2$, and at least one of $R^A$ and $R^B$ is H; and $R^1$ is defined as in formula (III) above;

in the presence of a base to obtain an aryloxyacetamide of formula (I-1); and (ii) reacting the aryloxyacetamide of formula (I-1) with $HNO_3/H_2SO_4$.

The phenol of formula (III-1) that is converted into the alpha-aryloxyacetamide of formula (I-1) can also be used in the form of a salt, preferably in the form of its sodium, potassium, magnesium or calcium salt.

Especially preferred the alkali metal or alkaline metal salts of the phenols of formula (III-1) as described herein are used.

If a salt of the phenol of formula (III-1) is used, the addition of a base is not necessary.

Dinitro compounds of formula (I-2) (corresponding to aryloxyacetamides of formula (I), wherein $R^A$ and $R^B$ are $NO_2$) are useful in the synthesis of NH-benzoxazinones of formula (V-1):

NH-benzoxazinones of formula (V-1) can be prepared by reaction of dinitro compounds of formula (I-2) with a reducing agent to obtain diamino compounds of formula (VI), which are treated with an acid:

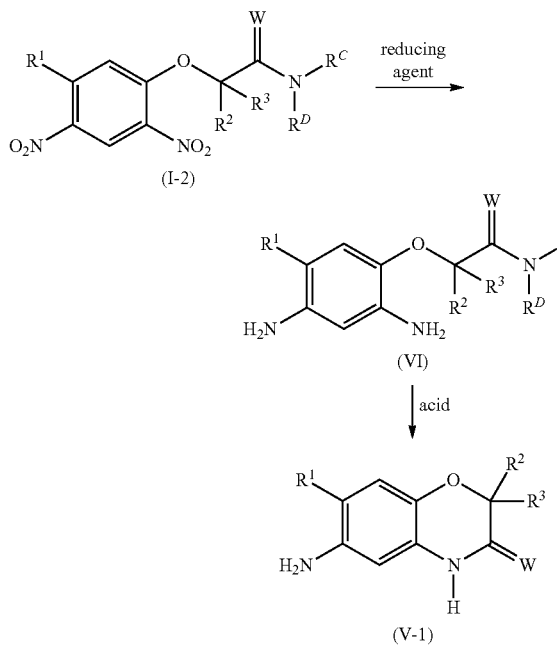

wherein
$R^1$, $R^2$, $R^3$, $R^C$, $R^D$ and W are defined as in formula (I) above.

Accordingly, in a further preferred embodiment of the process of the invention the NH-benzoxazinones of formula (V-1) are prepared by
i) reacting an haloacetamide of formula (II) with a phenol of formula (III-1) in the presence of a base to obtain an aryloxyacetamide of formula (I-3),

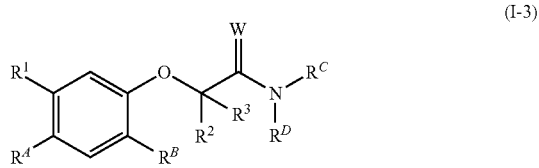

wherein
$R^A$, $R^B$ are independently H or $NO_2$; and
$R^1$, $R^2$, $R^3$, $R^C$, $R^D$ and W are defined as in formula (I) above;
ii) if $R^A$ and/or $R^B$ in formula (I-3) are H, i.e. the compound of formula (I-3) is a compound of formula (I-1): reacting the aryloxyacetamide of formula (I-3) with $HNO_3/H_2SO_4$ to obtain a dinitro compound of formula (I-2);
iii) reacting the dinitro compound of formula (I-2) with a reducing agent to obtain a diamino compound of formula (VI); and
iv) treating the diamino compound of formula (VI) with an acid to obtain the NH-benzoxazinone of formula (V-1).

The phenol of formula (III-1) that is converted into the aryloxyacetamide of formula (I-3) can also be used in the form of a salt, preferably in the form of its sodium, potassium, magnesium or calcium salt. If a salt of the phenol of formula (III-1) is used, the addition of a base is not necessary.

NH-benzoxazinones of formula (V-1) are useful in the synthesis of 4-substituted amino-benzoxazinones of formula (V-2):

The 4-substituted amino-benzoxazinones of formula (V-2) can be prepared by reacting NH-benzoxazinones of formula (V-1) with a base and a compound of formula (VII), $R^\#L^\#$:

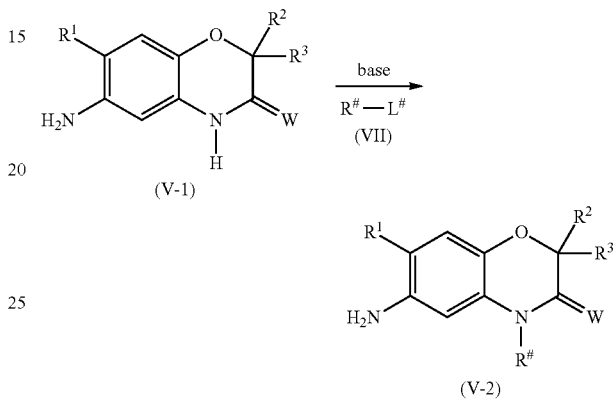

wherein
$R^\#$ is $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
$L^\#$ is halogen or $OS(O)_2R^7$;
$R^7$ is $C_1$-$C_6$-alkyl, $C_1$-$C_6$-haloalkyl, $C_1$-$C_6$-nitroalkyl, $C_1$-$C_6$-alkoxy-$C_1$-$C_6$-alkyl, $C_3$-$C_6$-cycloalkyl, phenyl or phenyl-$C_1$-$C_6$-alkyl, wherein each phenyl ring independently of one another is unsubstituted or substituted by 1 to 5 substituents selected from the group consisting of halogen, CN, $NO_2$, $C_1$-$C_6$-alkyl, $C_1$-$C_6$-haloalkyl or $C_1$-$C_6$-alkoxy; and
$R^1$, $R^2$, $R^3$ and W are defined as in formula (I) above.

The NH-benzoxazinone of formula (V-1) that is converted into the 4-substituted amino-benzoxazinone of formula (V-2) can also be used in the form of a salt, for example in form of its alkali metal or alkaline metal salt, preferably in the form of its lithium, sodium or potassium salt. If a salt of the NH-benzoxazinone of formula (V-1) is used, the addition of a base is not necessary.

The compounds of formula (VII), $R^\#$-$L^\#$, necessary for the preparation of the 4-substituted amino-benzoxazinone of formula (V-2), are commercially available, or can be prepared by methods known in the art, e.g. Houben-Weyl 1985, E11-2, p. 1084.

Accordingly, in a further preferred embodiment of the process of the invention 4-substituted amino-benzoxazinones of formula (V-2) are prepared by
i) reacting an haloacetamide of formula (II) with a phenol of formula (III-1) in the presence of a base to obtain an aryloxyacetamide of formula (I-3);
ii) if $R^A$ and/or $R^B$ in formula (I-3) are H, i.e. the compound of formula (I-3) is a compound of formula (I-1): reacting the aryloxyacetamide of formula (I-3) with $HNO_3/H_2SO_4$ to obtain a dinitro compound of formula (I-2);

iii) reacting the dinitro compound of formula (I-2) with a reducing agent to obtain a diamino compound of formula (VI);
iv) treating the diamino compound of formula (VI) with an acid to obtain a NH-benzoxazinone of formula (V-1); and
v) reacting the NH-benzoxazinone of formula (V-1) with a base and a compound of formula (VII).

The term "amino-benzoxazinones of formula (V)" combines NH-benzoxazinones of formula (V-1) and 4-substituted amino-benzoxazinones of formula (V-2):

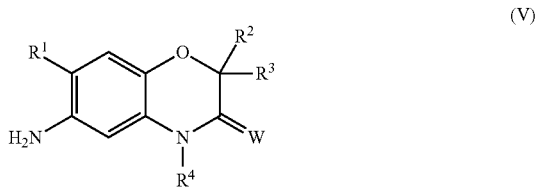

(V)

wherein
R$^4$ is hydrogen, C$_1$-C$_6$-alkyl, C$_1$-C$_6$-haloalkyl, C$_3$-C$_6$-cycloalkyl, C$_3$-C$_6$-alkenyl, C$_3$-C$_6$-haloalkenyl, C$_3$-C$_6$-alkynyl, C$_3$-C$_6$-haloalkynyl, C$_1$-C$_6$-alkoxy or C$_3$-C$_6$-cycloalkyl-C$_1$-C$_6$-alkyl; and
R$^1$, R$^2$, R$^3$ and W are defined as in formula (I) above.

Accordingly, NH-benzoxazinones of formula (V-1) correspond to amino-benzoxazinones of formula (V), wherein R$^4$ is hydrogen.

Accordingly, amino-benzoxazinones of formula (V-2) correspond to amino-benzoxazinones of formula (V), wherein R$^4$ is R$^\#$, which is C$_1$-C$_6$-alkyl, C$_1$-C$_6$-haloalkyl, C$_3$-C$_6$-cycloalkyl, C$_3$-C$_6$-alkenyl, C$_3$-C$_6$-haloalkenyl, C$_3$-C$_6$-alkynyl, C$_3$-C$_6$-haloalkynyl, C$_1$-C$_6$-alkoxy or C$_3$-C$_6$-cycloalkyl-C$_1$-C$_6$-alkyl.

Amino-benzoxazinones of formula (V) are useful in the synthesis of triazinon-benzoxazinones of formula (IV):

Triazinon-benzoxazinones of formula (IV) can be prepared by reacting amino-benzoxazinones of formula (V) with 1,1'-carbonyldiimidazole (CDI) and a (thio)urea compound of formula (VIII):

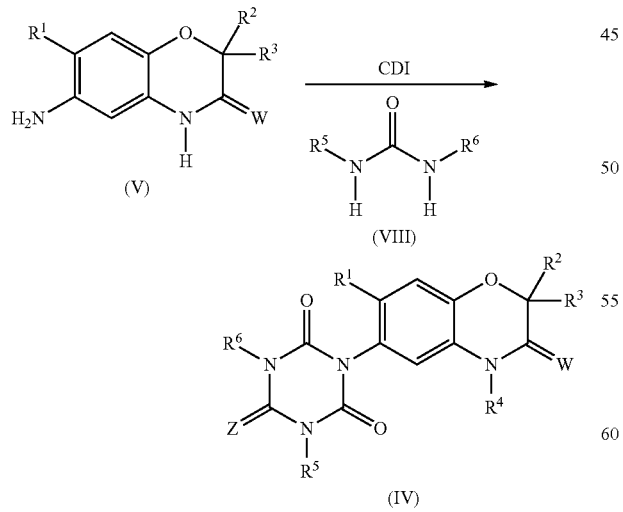

wherein
R$^1$, R$^2$, R$^3$, R$^4$, R$^5$, R$^6$, W and Z are defined as in formula (IV) above.

Preferably, the reaction of the amino-benzoxazinone of formula (V) with 1,1'-carbonyldiimidazole (CDI) and the (thio)urea compound of formula (VIII) to obtain the triazinon-benzoxazinone of formula (IV) is carried out in the presence of a base.

Accordingly, in a further preferred embodiment of the process of the invention triazinon-benzoxazinones of formula (IV) are prepared by i) reacting an haloacetamide of formula (II) with a phenol of formula (III-1) in the presence of a base to obtain an aryloxyacetamide of formula (I-3)
ii) if R$^A$ and/or R$^B$ in formula (I-3) are H, i.e. the compound of formula (I-3) is a compound of formula (I-1): reacting the aryloxyacetamide of formula (I-3) with HNO$_3$/H$_2$SO$_4$ to obtain a dinitro compound of formula (I-2);
iii) reacting the dinitro compound of formula (I-2) with a reducing agent to obtain a diamino compound of formula (VI);
iv) treating the diamino compound of formula (VI) with an acid to obtain a NH-benzoxazinone of formula (V-1);
v) optionally reacting the NH-benzoxazinone of formula (V-1) with a base and a compound of formula (VII) to obtain a 4-substituted amino-benzoxazinone of formula (V-2); and
vi) reacting the amino-benzoxazinone of formula (V) with 1,1'-carbonyldiimidazole (CDI) and a (thio)urea compound of formula (VIII).

In another embodiment of the process according to the invention the aryloxyacetamide of formula (I-3) is further converted into a triazinon-benzoxazinone of formula (IV),

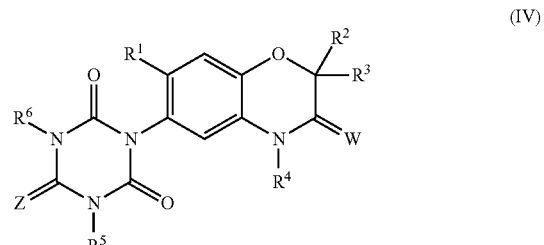

(IV)

wherein
R$^1$ is H or halogen;
R$^2$ is halogen;
R$^3$ is H or halogen;
R$^4$ is H, C$_1$-C$_6$ alkyl, C$_1$-C$_6$ haloalkyl, C$_3$-C$_6$ cycloalkyl, C$_3$-C$_6$ alkenyl, C$_3$-C$_6$ haloalkenyl, C$_3$-C$_6$ alkynyl, C$_3$-C$_6$ haloalkynyl, C$_1$-C$_6$ alkoxy or C$_3$-C$_6$-cycloalkyl-C$_1$-C$_6$-alkyl;
R$^5$ is H, NH$_2$, C$_1$-C$_6$ alkyl or C$_3$-C$_6$ alkynyl;
R$^6$ is H or C$_1$-C$_6$ alkyl;
W is O; and
Z is O or S;
by
ii) if R$^A$ and/or R$^B$ in formula (I-3) are H:
reacting the alpha-aryloxyacetamide of formula (I-3) with HNO$_3$/H$_2$SO$_4$ to obtain a dinitro compound of formula (I-2),

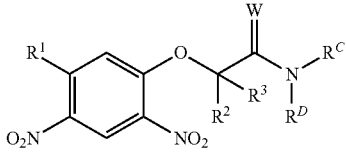

(I-2)

wherein $R^1$, $R^2$, $R^3$ and W are defined as in formula (IV); and $R^C$ and $R^D$ are defined as in formula (I-3);

iii) reacting the dinitro compound of formula (I-2) with a reducing agent to obtain a diamino compound of formula (VI);

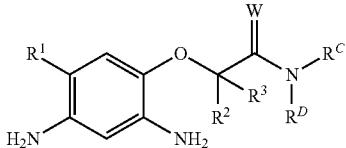

(VI)

wherein $R^1$, $R^2$, $R^3$ and W are defined as in formula (IV); and $R^C$ and $R^D$ are defined as in formula (I-3);

iv) treating the diamino compound of formula (VI) with an acid to obtain a NH-benzoxazinone of formula (V-1),

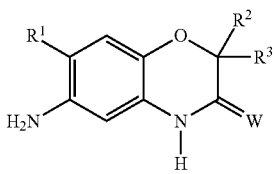

(V-1)

wherein $R^1$, $R^2$, $R^3$ and W are defined as in formula (IV);

v) optionally reacting the NH-benzoxazinone of formula (V-1) with a base and a compound of formula (VII), $R^\#\text{-}L^\#$ (VII)

wherein $R^\#$ is $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;

$L^\#$ is halogen or $OS(O)_2R^7$; and $R^7$ is $C_1$-$C_6$-alkyl, $C_1$-$C_6$-haloalkyl, $C_1$-$C_6$-nitroalkyl, $C_1$-$C_6$-alkoxy-$C_1$-$C_6$-alkyl, $C_3$-$C_6$-cycloalkyl, phenyl or phenyl-$C_1$-$C_6$-alkyl, wherein each phenyl ring independently of one another is unsubstituted or substituted by 1 to 5 substituents selected from the group consisting of halogen, CN, $NO_2$, $C_1$-$C_6$-alkyl, $C_1$-$C_6$-haloalkyl or $C_1$-$C_6$-alkoxy;

to obtain a 4-substituted amino-benzoxazinone of formula (V-2),

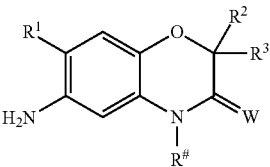

(V-2)

wherein $R^1$, $R^2$, $R^3$ and W are defined as in formula (IV); and $R^\#$ is defined as in formula (VII); and vi) reacting the amino-benzoxazinone of formula (V),

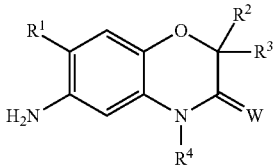

(V)

wherein $R^1$, $R^2$, $R^3$ and W are defined as in formula (IV); and $R^4$ is H or R# as defined in formula (VII);

with 1,1'-carbonyldiimidazole (CDI) and a (thio)urea compound of formula (VIII),

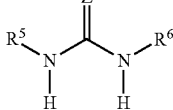

(VIII)

wherein $R^5$, $R^6$ and Z are defined as in formula (IV);

to obtain the triazinon-benzoxazinone of formula (IV).

In a preferred embodiment step vi) is carried out in the presence of a base.

With respect to the variables within the compounds of formulae (I-1), (I-2), (I-3), (III-1), (IV), (V), (V-1), (V-2), (VI), (VII) or (VIII), the particularly preferred embodiments of the compounds of formulae (I-1), (I-2), (I-3), (III-1), (IV), (V), (V-1), (V-2), (VI), (VII) or (VIII) correspond, either independently of one another or in combination with one another, to those of the variables of $R^1$, $R^2$, $R^3$, $R^C$, $R^D$, W and L of formulae (I), (II) or (III), or have, either independently of one another or in combination with one another, the following meanings:

$R^4$ is preferably $C_3$-$C_6$-alkynyl or $C_3$-$C_6$-haloalkynyl, more preferably $C_3$-alkynyl or $C_3$-haloalkynyl, particularly preferred $CH_2C\equiv CH$, $CH_2C\equiv CCl$ or $CH_2C\equiv CBr$;

is also preferably $C_3$-$C_6$-alkynyl or $C_3$-$C_6$-cycloalkyl-$C_1$-$C_6$-alkyl, particularly preferred propargyl or cyclopropylmethyl;

is also preferably $C_3$-$C_6$-alkynyl, more preferably $C_3$-alkynyl; particularly preferred $CH_2C\equiv CH$;

is also preferably $C_3$-$C_6$-haloalkynyl, more preferably $C_3$-haloalkynyl, particularly preferred $CH_2C\equiv CCl$ or $CH_2C\equiv CBr$;

$R^5$ is preferably $NH_2$, $C_1$-$C_6$-alkyl or $C_3$-$C_6$-alkynyl; also preferably H or $C_1$-$C_6$-alkyl; more preferably $C_1$-$C_6$-alkyl; most preferably $C_1$-$C_4$-alkyl; particularly preferred $CH_3$;

$R^6$ is preferably $C_1$-$C_6$-alkyl; more preferably $C_1$-$C_4$-alkyl; most preferably $CH_3$;

Z is preferably O,
is also preferably S;

$R^\#$ is preferably $C_3$-$C_6$-alkynyl or $C_3$-$C_6$-haloalkynyl, more preferably $C_3$-alkynyl or $C_3$-haloalkynyl, particularly preferred $CH_2C\equiv CH$, $CH_2C\equiv CCl$ or $CH_2C\equiv CBr$;
  is also preferably $C_3$-$C_6$-alkynyl or $C_3$-$C_6$-cycloalkyl-$C_1$-$C_6$-alkyl, particularly preferred propargyl or cyclopropylmethyl;
  is also preferably $C_3$-$C_6$-alkynyl, more preferably $C_3$-alkynyl; particularly preferred $CH_2C\equiv CH$;
  is also preferably $C_3$-$C_6$-haloalkynyl, more preferably $C_3$-haloalkynyl, particularly preferred $CH_2C\equiv CCl$ or $CH_2C\equiv CBr$;

$L\#$ is preferably halogen or $OS(O_2)R^7$,
  wherein $R^7$ is $C_1$-$C_6$-alkyl, phenyl or phenyl-$C_1$-$C_6$-alkyl, wherein each phenyl ring independently of one another is unsubstituted or substituted by 1 to 3 $C_1$-$C_6$-alkyl substituents;
  particularly preferred halogen or $OS(O_2)R^7$,
    wherein $R^7$ is $C_1$-$C_6$-alkyl or phenyl, wherein the phenyl ring is unsubstituted or substituted by 1 to 3 $C_1$-$C_6$-alkyl substituents;
  especially preferred Cl, Br, $OS(O)_2CH_3$ or $OS(O)_2(C_6H_4)CH_3$.

The invention is illustrated by the following examples without being limited thereto or thereby.

1. Preparation of Haloacetamides of Formula (II)

EXAMPLE 1.1

2-bromo-2,2-difluoro-N,N-dimethyl-acetamide

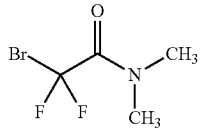

To a solution of ethyl bromodifluoroacetate (370 g, 1.82 mol) in 1000 mL of THF was added a solution of $Me_2NH$ in THF (2.0 M, 1000 mL, 2.0 mol). A slightly exothermic reaction occurred. The solution was stirred at room temperature overnight. The solvent was then carefully removed by distillation and the residue purified by rectification. The product was obtained as a colorless liquid (343 g, >99% pure by GC, 1.7 mol, 93% yield).

$^1$H NMR (DMSO-$d_6$, 500 MHz): δ (ppm)=3.18 (s, 3H), 3.02 (s, 3H). $^{13}$C NMR (DMSO-$d_6$, 125 MHz): δ (ppm)=158.6 (t, J=25 Hz); 110.5 (t, J=311 Hz); 37.3; 36.7. Boiling point: 71-76° C. (56 mbar)

EXAMPLE 1.2

2-bromo-2,2-difluoro-N, N-diethyl-acetamide

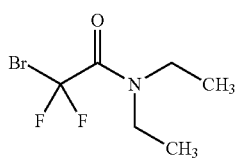

$Et_2NH$ (7.9 g, 108 mmol) was added to ethyl bromodifluoroacetate (20.1 g, 99 mmol) at 30° C. The mixture was stirred for 60 min; then all volatiles were removed under reduced pressure. To the residue was added another 7.9 g of $Et_2NH$ and the mixture was stirred another 60 min.

Again, all volatiles were removed under reduced pressure and the residue (16.3 g, >90% purity by NMR) was used in subsequent steps without further purification.

$^1$H NMR (CDCl$_3$, 500 MHz): δ (ppm)=3.53 (q, J=7.0 Hz, 2H); 3.43 (q, J=7.0 Hz, 2H); 1.26 (t, J=7.0 Hz, 3H); 1.20 (t, J=7.0 Hz, 3H).

$^{13}$C NMR (CDCl$_3$, 125 MHz): δ (ppm)=158.7 (t, J=26 Hz); 111.2 (t, J=313 Hz); 43.0; 42.1; 13.9; 11.9.

EXAMPLE 1.3

2-bromo-2,2-difluoro-1-pyrrolidine-1-yl-ethanone

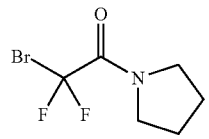 [SMILES: O=C(N1CCCC1)C(F)(F)Br]

Pyrrolidine (7.7 g, 108 mmol) was added to ethyl bromodifluoroacetate (20.2 g, 100 mmol) at 30° C. The mixture was stirred for 60 min; then all volatiles were removed under reduced pressure and the residue (24.0 g, >90% purity by NMR) was used in subsequent steps without further purification.

$^1$H NMR (CDCl$_3$, 500 MHz): δ (ppm)=3.66 (t, J=7.0 Hz, 2H); 3.58 (t, J=7.0 Hz, 2H); 2.03 (tt, J=7.0 Hz, J=7.0 Hz, 2H); 1.92 (tt, J=7.0 Hz, J=7.0 Hz, 2H).

$^{13}$C NMR (CDCl$_3$, 125 MHz): δ (ppm)=158.0 (t, J=28 Hz); 111.4 (t, J=313 Hz); 48:0, 47:7, 26:5, 23:4.

EXAMPLE 1.4

2-bromo-2,2-difluoro-N-isopropyl-N-methyl-acetamide

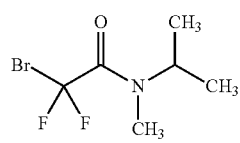

Methylisopropylamine (7.9 g, 108 mmol) was added to ethyl bromodifluoroacetate (20.0 g, 99 mmol) at 30° C. The mixture was stirred for 60 min; then all volatiles were removed under reduced pressure. The residue (10.4 g, >90% purity by NMR) was used in subsequent steps without further purification.

52:48 mixture of rotamers $^1$H NMR (CDCl$_3$, 500 MHz): δ (ppm)=4.54-4.56 (m, 1H); 4.48-4.50 (m, 1H); 3.01 (s, 3H); 2.88 (s, 3H); 1.26 (d, J=7.0 Hz, 6H); 1.18 (d, J=7.0 Hz, 6H).

$^{13}$C NMR (CDCl$_3$, 125 MHz): δ (ppm)=158.8 (t, J=26 Hz); 111.4 (t, J=313 Hz); 110.8 (t, J=313 Hz); 49.0; 47.1; 29.0; 27.6; 19.9; 18.8.

EXAMPLE 1.5

2-bromo-2,2-difluoro-1-morpholine-1-yl-ethanone

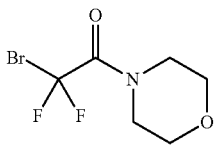

Morpholine (9.4 g, 108 mmol) was added to ethyl bromodifluoroacetate (20.0 g, 99 mmol) at 30° C. The mixture was stirred for 60 min; then all volatiles were removed under reduced pressure and the residue (13.0 g, >90% purity by NMR) was used in subsequent steps without further purification.

$^1$H NMR (CDCl$_3$, 500 MHz): δ (ppm)=3.75-3.82 (m, 4H); 3.63-3.69 (m, 4H).

$^{13}$C NMR (CDCl$_3$, 125 MHz): δ (ppm)=157.1 (t, J=26 Hz); 110.2 (t, J=310 Hz); 65.7; 65.4; 46.8; 43.4.

2. Preparation of aryloxyacetamides of formula (I)

EXAMPLE 2.1

2,2-difluoro-2-(3-fluoro-phenoxy)-N,N-dimethyl-acetamide

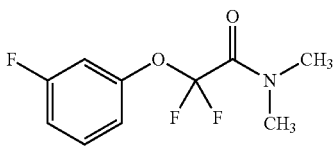 [SMILES: CN(C)C(=O)C(F)(F)Oc1cccc(F)c1]

A mixture of 3-fluoro-phenol (9.8 g, 87.4 mmol), 2-bromo-2,2-difluoro-N,N-dimethyl-acetamide (18.3 g, 89.6 mmol) and K$_2$CO$_3$ (13.3 g, 96.2 mmol) in 75 g of dimethylacetamide (DMAC) was heated to 100° C. for 1 h and then heated to 120° C. for 2 h. The reaction mixture was then cooled to room temperature and poured on 250 mL of H$_2$O and 50 mL of toluene. The aqueous phase was extracted with 25 g of toluene. The combined organic layers were extracted with 5% NaOH (20 g) and H$_2$O (2×20 g) and dried over Na$_2$SO$_4$. The product (18.5 g, >98% purity by quant. HPLC, 77.8 mmol, 89% yield) was obtained after removal of all volatiles under reduced pressure as a slightly yellow liquid. The material could be used in subsequent steps without further purification or purified by fractionated distillation.

$^1$H NMR (CDCl$_3$, 500 MHz): δ (ppm)=7.52-7.57 (m, 1H); 7.18-7.26 (m, 3H); 3.27 (s, 3H); 3.04 (s, 3H).

$^{13}$C NMR (CDCl$_3$, 125 MHz): δ (ppm)=162.9 (d, J=245 Hz); 158.3 (t, J=35 Hz); 150.3 (d, J=11 Hz); 131.6 (d, J=9 Hz); 117.6 (d, J=3 Hz); 115.7 (t, J=271 Hz); 113.8 (d, J=21 Hz); 109.5 (d, J=25 Hz); 37.1; 36.5.

Boiling point: 102° C. (0.5 mbar)

EXAMPLE 2.2

2,2-difluoro-2-(3-fluoro-phenoxy)-N,N-diethyl-acetamide

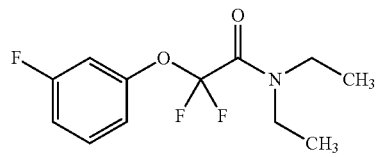 [SMILES: CCN(CC)C(=O)C(F)(F)Oc1cccc(F)c1]

To a mixture of 3-fluoro-phenol (4.9 g, 43.5 mmol), and K$_2$CO$_3$ (6.6 g, 47.8 mmol) in 43 g of DMAC at 100° C. was added 2-bromo-2,2-difluoro-N,N-diethyl-acetamide (10 g, 43.5 mmol). The mixture was kept at that temperature for 1 h and then heated to 120° C. for 2 h. The reaction mixture was then cooled to room temperature and poured on 120 mL of H$_2$O and 50 mL of toluene. The aqueous phase was extracted with 25 g of toluene. The combined organic layers were extracted with 5% NaOH (20 g) and H$_2$O (2×20 g) and dried over Na$_2$SO$_4$. The product (10.2 g, >90% purity by NMR) was obtained after removal of all volatiles under reduced pressure as a slightly yellow liquid. The material could be used in subsequent steps without further purification.

$^1$H NMR (CDCl$_3$, 500 MHz): δ (ppm)=7.31-7.36 (m, 1H); 7.02-7.05 (m, 1H); 6.95-6.99 (m, 2H); 3.58 (q, J=7.0 Hz, 2H); 3.45 (q, J=7.0 Hz, 2H); 1.26 (t, J=7.0 Hz, 3H); 1.18 (t, J=7.0 Hz, 3H).

$^{13}$C NMR (CDCl$_3$, 125 MHz): δ (ppm)=162.8 (d, J=246 Hz); 158.3 (t, J=31 Hz); 150.4 (d, J=10 Hz); 130.5 (d, J=9 Hz); 116.8 (d, J=3 Hz); 115.4 (t, J=273 Hz); 113.1 (d, J=21 Hz); 109.2 (d, J=25 Hz); 42.2; 41.5; 14.0; 12.2.

EXAMPLE 2.3

2,2-difluoro-2-(3-fluoro-phenoxy)-1-pyrrolidine-1-yl-ethanone

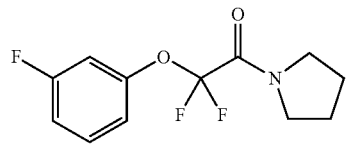 [SMILES: O=C(N1CCCC1)C(F)(F)Oc1cccc(F)c1]

To a mixture of 3-fluoro-phenol (4.5 g, 40.0 mmol), and K$_2$CO$_3$ (6.1 g, 44.0 mmol) in 40 g of DMAC at 100° C. was added 2-bromo-2,2-difluoro-1-pyrrolidine-1-yl-ethanone (9.1 g, 40.0 mmol). The mixture was kept at that temperature for 1 h and then heated to 120° C. for 2 h. The reaction mixture was then cooled to room temperature and poured on 120 mL of H$_2$O and 30 mL of toluene. The aqueous phase was extracted with 25 g of toluene. The combined organic layers were extracted with 10% NaOH (10 g) and H$_2$O (2×15 g) and dried over Na$_2$SO$_4$. The product (8.3 g, >90% purity by NMR) was obtained after removal of all volatiles under reduced pressure as a slightly yellow liquid. The material could be used in subsequent steps without further purification.

¹H NMR (CDCl₃, 500 MHz): δ (ppm)=7.32-7.36 (m, 1H); 7.02-7.06 (m, 1H); 6.95-7.00 (m, 2H); 3.76 (t, J=6.5 Hz, 2H); 3.59 (t, J=6.5 Hz, 2H); 1.98-2.03 (m, 2H); 1.88-1.94 (m, 2H).

¹³C NMR (CDCl₃, 125 MHz): δ (ppm)=162.8 (d, J=246 Hz); 157.6 (t, J=35 Hz); 150.4 (d, J=10 Hz); 130.5 (d, J=10 Hz); 117.0 (d, J=4 Hz); 115.3 (t, J=273 Hz); 113.2 (d, J=21 Hz); 109.3 (d, J=25 Hz); 47.4; 47.0; 26.4; 23.5.

EXAMPLE 2.4

2,2-difluoro-2-(3-fluoro-phenoxy)-N-isopropyl-N-methyl-acetamide

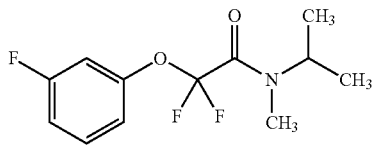 [SMILES: CC(C)N(C)C(=O)C(F)(F)Oc1cccc(F)c1]

To a mixture of 3-fluoro-phenol (4.9 g, 43.5 mmol), and K₂CO₃ (6.6 g, 47.8 mmol) in 46 mL of DMF at 100° C. was added 2-bromo-2,2-difluoro-N-isopropyl-N-methyl-acetamide (10 g, 43 mmol). The mixture was kept at that temperature for 1 h and then heated to 120° C. for 2 h. The reaction mixture was then cooled to room temperature and poured on 120 mL of H₂O and 30 mL of toluene. The aqueous phase was extracted with 30 mL of toluene. The combined organic layers were extracted with 10% NaOH (16 g) and H₂O (2×15 g) and dried over MgSO₄. The product (8.6 g, >90% purity by NMR) was obtained after removal of all volatiles under reduced pressure as a slightly yellow liquid. The material could be used in subsequent steps without further purification.

51:49 mixture of rotamers

¹H NMR (CDCl₃, 500 MHz): δ (ppm)=7.31-7.36 (m, 2H); 7.02-7.05 (m, 2H); 6.94-6.99 (m, 4H); 4.79 (sept., J=7.0 Hz, 1H); 4.53 (sept., J=7.0 Hz, 1H); 3.05 (s, 3H); 2.90 (s, 3H); 1.26 (d, J=7.0 Hz, 6H); 1.16 (d, J=7.0 Hz, 6H).

¹³C NMR (CDCl₃, 125 MHz): δ (ppm)=162.9 (d, J=246 Hz); 162.8 (d, J=246 Hz); 158.6 (t, J=35 Hz); 158.5 (t, J=35 Hz); 150.5; 150.4; 130.6 (d, J=9 Hz); 130.5 (d, J=9 Hz); 116.8 (d, J=3 Hz); 116.6 (d, J=3 Hz); 115.6 (t, J=273 Hz); 115.5 (t, J=273 Hz); 113.2 (d, J=21 Hz); 113.1 (d, J=21 Hz); 109.2 (d, J=25 Hz); 109.1 (d, J=25 Hz); 48.4; 46.4; 28.2; 27.3; 20.3; 18.9.

EXAMPLE 2.5

2,2-difluoro-2-(3-fluoro-phenoxy)-1-morpholino-1-yl-ethanone

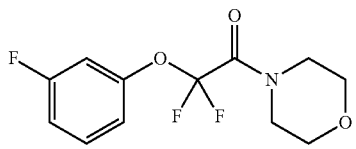 [SMILES: O=C(N1CCOCC1)C(F)(F)Oc1cccc(F)c1]

A mixture of 3-fluoro-phenol (5.6 g, 48.3 mmol), 2-bromo-2,2-difluoro-1-morpholine-1-yl-ethanone (11.7 g, 48 mmol) and K₂CO₃ (8.0 g, 57.9 mmol) in 50 g of DMAC was heated to 100° C. for 1 h and then heated to 120° C. for 2 h. The reaction mixture was then cooled to room temperature and poured on 250 mL of H₂O and 50 mL of toluene. The aqueous phase was extracted with 25 g of toluene. The combined organic layers were extracted with 5% NaOH (20 g) and H₂O (2×20 g) and dried over Na₂SO₄. The crude product was obtained after removal of all volatiles under reduced pressure as a slightly yellow liquid. The material could be used in subsequent steps without further purification.

¹H NMR (CDCl₃, 500 MHz): δ (ppm)=7.31-7.36 (m, 1H); 7.01-7.04 (m, 1H); 6.94-6.99 (m, 2H); 3.68-3.78 (m, 8H).

¹³C NMR (CDCl₃, 125 MHz): δ (ppm)=162.9 (t, J=246 Hz); 157.6 (t, J=35 Hz); 150.3 (d, J=11 Hz); 130.7 (d, J=9 Hz); 116.7 (d, J=4 Hz); 115.3 (t, J=273 HZ); 113.3 (d, J=20 Hz); 109.0 (d, J=25 Hz); 66.7; 66.6; 46.8; 43.6.

EXAMPLE 2.6

2,2-difluoro-2-(5-fluoro-2-nitro-phenoxy)-N,N-dimethyl-acetamide

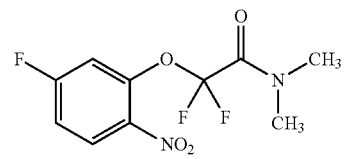 [SMILES: CN(C)C(=O)C(F)(F)Oc1cc(F)ccc1[N+](=O)[O-]]

A mixture of 2-nitro-5-fluoro-phenol (3.0 g, 19.1 mmol), 2-bromo-2,2-difluoro-N,N-dimethyl-acetamide (3.9 g, 19.1 mmol) and Na₂CO₃ (2.1 g, 19.8 mmol) in 30 mL of DMAC was heated to 100° C. overnight. The mixture was then poured on 50 mL of H₂O and extracted with TBME (2×50 mL). The combined organic layers were washed with 10% NaOH (50 mL) and dried over Na₂SO₄. The crude product was obtained after evaporation of all volatiles. Purification by chromatography on silica gave the product (1.8 g, 6.4 mmol, 38% yield) as a yellow oil that solidified upon standing.

¹H NMR (CDCl₃, 500 MHz): δ (ppm)=8.04 (dd, J=5.5 Hz, J=9.0 Hz, 1H); 7.26-7.29 (m, 1H); 7.13 (dd, J=2.5 Hz, J=7.5 Hz, 1H); 3.25 (s, 3H); 3.09 (s, 3H).

¹³C NMR (CDCl₃, 125 MHz): δ (ppm)=164.5 (d, J=258 Hz); 157.9 (t, J=34 Hz); 143.9 (d, J=11 Hz); 138.9; 127.9 (d, J=11 Hz); 115.5 (t, J=278 Hz); 113.6 (d, J=10 Hz); 110.9 (d, J=28 Hz); 37.2; 37.1.

EXAMPLE 2.7

2,2-difluoro-2-(2-bromo-5-fluoro-henoxy)-N,N-dimethyl-acetamide

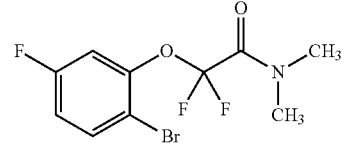 [SMILES: CN(C)C(=O)C(F)(F)Oc1cc(F)ccc1Br]

A mixture of 2-bromo-5-fluoro-phenol (4.0 g, 20.7 mmol), 2-bromo-2,2-difluoro-N,N-dimethyl-acetamide (4.4 g, 21.6 mmol) and K₂CO₃ (3.2 g, 23.2 mmol) in 20 mL of DMAC was heated to 100° C. for 120 min. The mixture was then poured on 50 mL of H₂O and extracted with TBME (2×50 mL). The combined organic layers were washed with 10%

NaOH (50 mL), water and brine and dried over MgSO$_4$. The product (5.9 g, >97% purity by NMR, 18.9 mmol, 91% yield) was obtained as a yellow oil that solidified upon standing.

$^1$H NMR (CDCl$_3$, 400 MHz): δ (ppm)=7.56 (dd, J=6.0 Hz, J=8.8 Hz, 1H); 7.13-7.17 (m, 1H); 6.87 (dd, J=2.8 Hz, J=7.6 Hz, 1H); 3.28 (s, 3H); 3.07 (s, 3H).

$^{13}$C NMR (CDCl$_3$, 100 MHz): δ (ppm)=161.7 (d, J=248 Hz); 158.5 (t, J=34 Hz); 147.5 (d, J=11 Hz); 134.2 (d, J=9 Hz); 115.5 (t, J=275 Hz); 114.3 (d, J=28 Hz); 110.2 (d, J=27 Hz); 109.8 (d, J=21 Hz); 37.5; 37.0.

EXAMPLE 2.8

2,2-difluoro-2-(4-bromo-5-fluoro-phenoxy)-N,N-dimethyl-acetamide

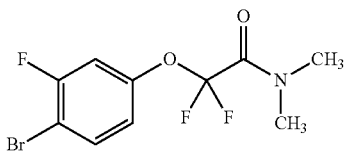 [SMILES: CN(C)C(=O)C(F)(F)Oc1ccc(Br)c(F)c1]

A mixture of 4-bromo-5-fluoro-phenol (4.0 g, 20.7 mmol), 2-bromo-2,2-difluoro-N,N-dimethyl-acetamide (4.4 g, 21.6 mmol) and K$_2$CO$_3$ (3.2 g, 23.2 mmol) in 20 mL of DMAC was heated to 100° C. for 120 min. The mixture was then poured on 50 mL of H$_2$O and extracted with TBME (2×50 mL). The combined organic layers were washed with 10% NaOH (50 mL), water and brine and dried over MgSO$_4$. The product (5.7 g, >96% purity by NMR, 17.6 mmol, 85% yield) was obtained as a yellow oil that solidified upon standing.

$^1$H NMR (CDCl$_3$, 400 MHz): δ (ppm)=7.52 (dd, J=8.0 Hz, J=8.8 Hz, 1H); 7.03 (dd, J=2.4 Hz, J=8.8 Hz, 1H); 6.91-6.95 (m, 1H); 3.21 (s, 3H); 3.04 (s, 3H).

$^{13}$C NMR (CDCl$_3$, 100 MHz): δ (ppm)=159.0 (d, J=248 Hz); 158.6 (t, J=35 Hz); 149.5 (d, J=10 Hz); 133.8; 118.0 (d, J=4 Hz); 115.3 (t, J=274 Hz); 110.2 (d, J=26 Hz); 106.1 (d, J=21 Hz); 37.2; 36.9.

The invention claimed is:

1. A process for manufacturing aryloxyacetamides of formula (I),

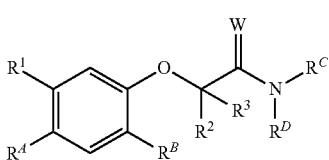

wherein
R$^1$ is H or halogen;
R$^2$ is halogen;
R$^3$ is H or halogen;
R$^A$ is selected from the group consisting of H, halogen, NH$_2$ and NO$_2$;
R$^B$ is selected from the group consisting of H, halogen, NH$_2$ and NO$_2$;
1. R$^C$, R$^D$ are independently of each other selected from the group consisting of C$_1$-C$_6$-alkyl, C$_2$-C$_6$-alkenyl, C$_2$-C$_6$-alkynyl, C$_1$-C$_6$-haloalkyl, C$_1$-C$_6$-cyanoalkyl, C$_1$-C$_6$-nitroalkyl, C$_1$-C$_6$-hydroxyalkyl, C$_1$-C$_6$-alkoxy-C$_1$-C$_6$-alkyl, amino-C$_1$-C$_6$-alkyl, di(C$_1$-C$_6$-alkyl)amino-C$_1$-C$_6$-alkyl, C$_3$-C$_6$-cycloalkyl, phenyl and benzyl, wherein the phenyl and the benzyl ring are independently of one another unsubstituted or substituted by 1 to 5 substituents selected from the group consisting of halogen, NO$_2$, C$_1$-C$_6$-alkyl and C$_1$-C$_6$-alkoxy, or R$^C$ and R$^D$ together with the N atom which they are attached to, represent a saturated or aromatic 3- to 6-membered ring, optionally containing 1 to 3 additional heteroatoms selected from the group consisting of O, S and N, with the ring optionally being substituted with 1 to 3 C$_1$-C$_6$-alkyl substituents; and W is O;
wherein haloacetamides of formula (II),

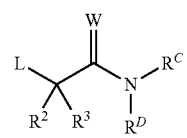

wherein R$^2$, R$^3$, R$^C$, R$^D$ and W are defined as in formula (I); and
L is halogen;
are reacted with a phenol of formula (III),

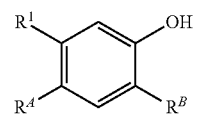

or a salt thereof,
wherein R$^1$, R$^A$ and R$^B$ are defined as in formula (I);
in the presence of a base.

2. The process of claim 1, wherein a phenol of formula (III) is employed and the reaction of the haloacetamide of formula (II) with the phenol of formula (III) is carried out in the presence of a base.

3. The process of claim 1, wherein a salt of the phenol of formula (III) is employed.

4. The process of claim 1, wherein R$^A$, R$^B$ are independently H or NO$_2$, for preparing an aryloxyacetamide of formula (I-3),

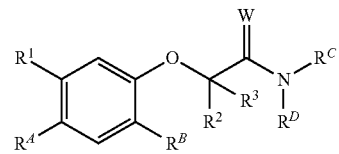

wherein
R$^1$ is H or halogen;
R$^2$ is halogen;
R$^3$ is H or halogen;
R$^A$ is H or NO$_2$;
R$^B$ is H or NO$_2$;
R$^C$, R$^D$ are independently of each other selected from the group consisting of C$_1$-C$_6$-alkyl, C$_2$-C$_6$-alkenyl, C$_2$-C$_6$- alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, di($C_1$-$C_6$-alkyl)amino-$C_1$-$C_6$-alkyl, $C_3$-$C_6$-cycloalkyl, phenyl and benzyl, wherein the phenyl and the benzyl ring are independently of one another unsubstituted or substituted by 1 to 5 substituents selected from the group consisting of halogen, $NO_2$, $C_1$-$C_6$-alkyl and $C_1$-$C_6$-alkoxy, or $R^C$ and $R^D$ together with the N atom which they are attached to, represent a saturated or aromatic 3- to 6-membered ring, optionally containing 1 to 3 additional heteroatoms selected from the group consisting of O, S and N, with the ring optionally being substituted with 1 to 3 $C_1$-$C_6$-alkyl substituents; and W is O.

5. Aryloxyacetamides of formula (I),

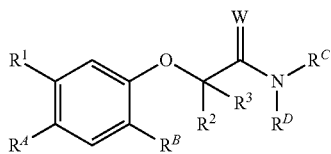

wherein
$R^1$ is fluoro;
$R^2$ is halogen;
$R^3$ is H or halogen;
$R^A$ is selected from the group consisting of H, halogen, $NH_2$ and $NO_2$;
$R^B$ is selected from the group consisting of H, halogen, $NH_2$ and $NO_2$;
$R^C$, $R^D$ are independently of each other selected from the group consisting of $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl and benzyl, wherein the phenyl and the benzyl ring are independently of one another unsubstituted or substituted by 1 to 5 substituents selected from the group consisting of halogen, $NO_2$, $C_1$-$C_6$-alkyl and $C_1$-$C_6$-alkoxy, or $R^C$ and $R^D$ together with the N atom which they are attached to, represent a saturated or aromatic 3- to 6-membered ring, optionally containing 1 to 3 additional heteroatoms selected from the group consisting of O, S and N, with the ring optionally being substituted with 1 to 3 $C_1$-$C_6$-alkyl substituents; and W is O.

6. The aryloxyacetamide of formula (I) of claim 5, wherein $R^3$ is halogen.

7. The aryloxyacetamide of formula (I) of claim 5, wherein $R^A$ and $R^B$ are H.

8. The aryloxyacetamide of formula (I) of claim 5, wherein $R^C$ and $R^D$ are $C_1$-$C_6$-alkyl.

* * * * *